(12) United States Patent
Toyoda et al.

(10) Patent No.: US 10,180,317 B2
(45) Date of Patent: Jan. 15, 2019

(54) PATTERN-MEASURING DEVICE AND COMPUTER PROGRAM

(71) Applicant: Hitachi High-Technologies Corporation, Minato-ku, Tokyo (JP)

(72) Inventors: Yasutaka Toyoda, Tokyo (JP); Hiroyuki Sindo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 122 days.

(21) Appl. No.: 15/117,964

(22) PCT Filed: Jan. 7, 2015

(86) PCT No.: PCT/JP2015/050195
§ 371 (c)(1),
(2) Date: Aug. 10, 2016

(87) PCT Pub. No.: WO2015/125504
PCT Pub. Date: Aug. 27, 2015

(65) Prior Publication Data
US 2016/0356598 A1  Dec. 8, 2016

(30) Foreign Application Priority Data
Feb. 21, 2014 (JP) ................. 2014-031203

(51) Int. Cl.
*G01B 15/00* (2006.01)
*G01N 23/203* (2006.01)
(Continued)

(52) U.S. Cl.
CPC ........... *G01B 15/00* (2013.01); *G01N 23/203* (2013.01); *G01N 23/2251* (2013.01);
(Continued)

(58) Field of Classification Search
CPC ..................................... G01B 15/00
See application file for complete search history.

(56) References Cited

U.S. PATENT DOCUMENTS 8,019,161 B2  9/2011 Morokuma et al.
8,045,785 B2  10/2011 Kitamura et al.
(Continued)

FOREIGN PATENT DOCUMENTS

JP  2002-93875 A  3/2002
JP  2002-148031 A  5/2002
(Continued)

OTHER PUBLICATIONS

International Search Report (PCT/ISA/210) issued in PCT Application No. PCT/JP2015/050195 dated Apr. 14, 2015 with English translation (3 pages).

(Continued)

*Primary Examiner* — Manuel A Rivera Vargas
(74) *Attorney, Agent, or Firm* — Crowell & Moring LLP

(57) ABSTRACT

In order to provide a pattern-measuring device and a computer program that quantitatively evaluate the effects brought about by the presence of pattern deformations in a circuit, this invention proposes a pattern-measuring device that measures first distances between first edges in pattern data being measured and second edges that correspond to said first edges in a benchmark pattern that corresponds to the pattern being measured. Said pattern-measuring device computes a score for the first edges or the pattern being measured on the basis of the first distances and second distances between the first edges and/or the second edges and third edges that are adjacent to but different from the first and second edges.

7 Claims, 15 Drawing Sheets

(51) Int. Cl.
*G01N 23/2251* (2018.01)
*H01L 21/66* (2006.01)

(52) U.S. Cl.
CPC .. *G01B 2210/56* (2013.01); *G01N 2223/6116* (2013.01); *H01L 22/12* (2013.01)

(56) References Cited

U.S. PATENT DOCUMENTS

| | | | |
|---|---|---|---|
| 2002/0030187 A1 | 3/2002 | Noda et al. | |
| 2006/0245636 A1 | 11/2006 | Kitamura et al. | |
| 2008/0069452 A1* | 3/2008 | Matsumoto | G06K 9/00 |
| | | | 382/207 |
| 2009/0052765 A1 | 2/2009 | Toyoda et al. | |
| 2010/0327160 A1* | 12/2010 | Zhao | H01J 37/265 |
| | | | 250/307 |
| 2012/0053892 A1* | 3/2012 | Matsuoka | B82Y 10/00 |
| | | | 702/167 |
| 2012/0068065 A1* | 3/2012 | Mitsui | H01J 37/222 |
| | | | 250/307 |

FOREIGN PATENT DOCUMENTS

| | | |
|---|---|---|
| JP | 2004-163420 A | 6/2004 |
| JP | 2007-149055 A | 6/2007 |
| JP | 2007-248087 A | 9/2007 |
| JP | 2009-71271 A | 4/2009 |

OTHER PUBLICATIONS

Japanese-language Written Opinion (PCT/ISA/237) issued in PCT Application No. PCT/JP2015/050195 dated Apr. 14, 2015 (3 pages).

* cited by examiner

[Fig. 1]
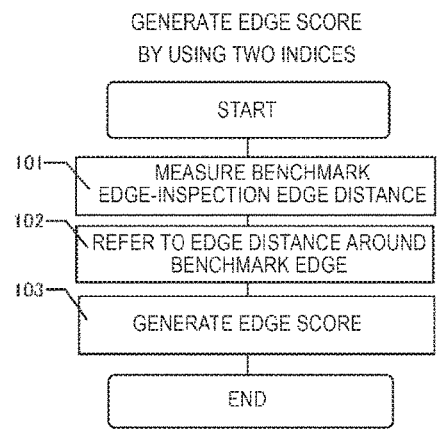
[Fig. 2]
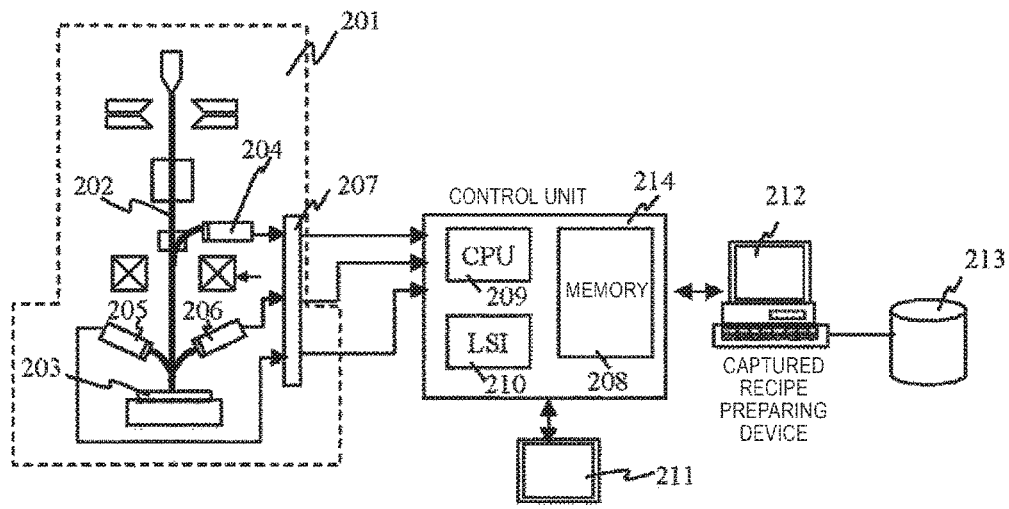

[Fig. 4]

[Fig. 5]
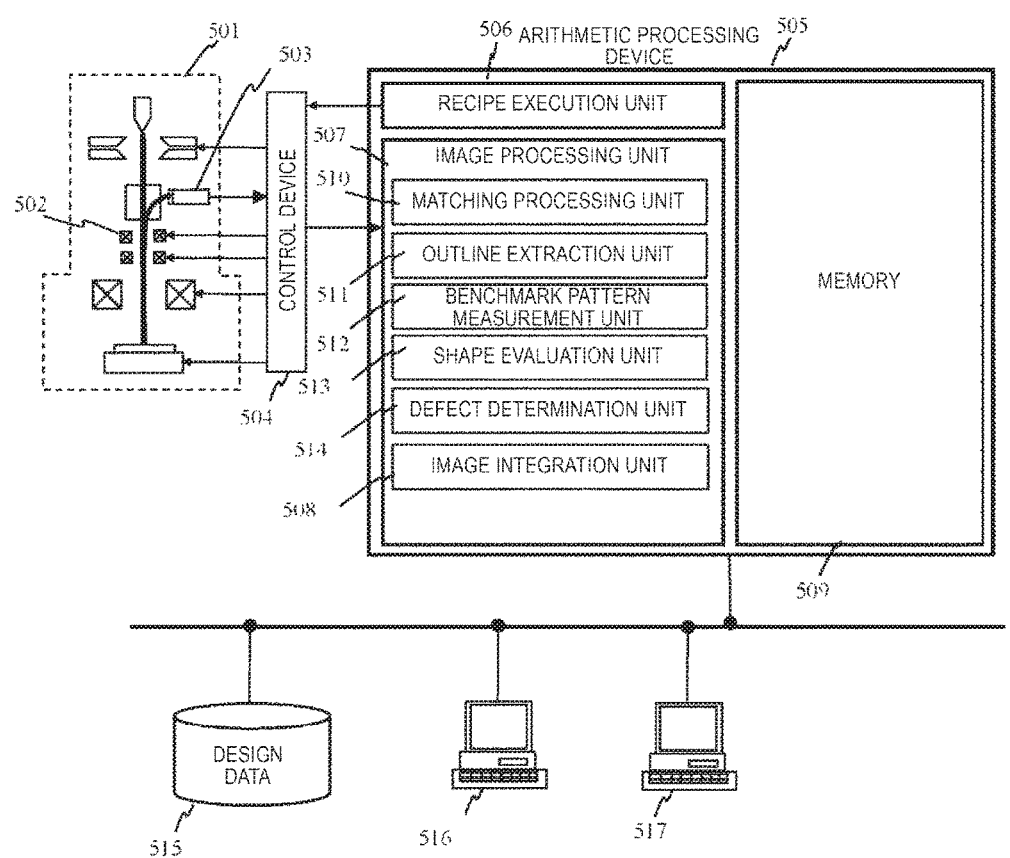

[Fig. 6]
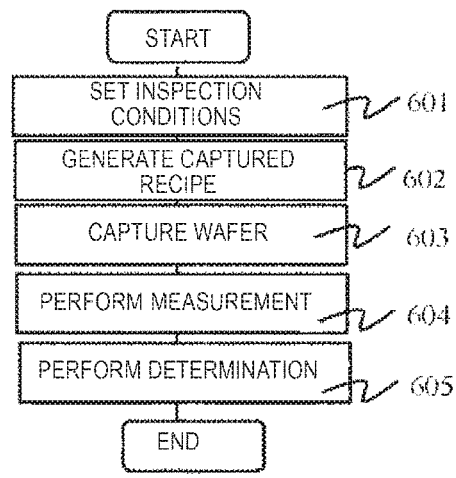
[Fig. 7]
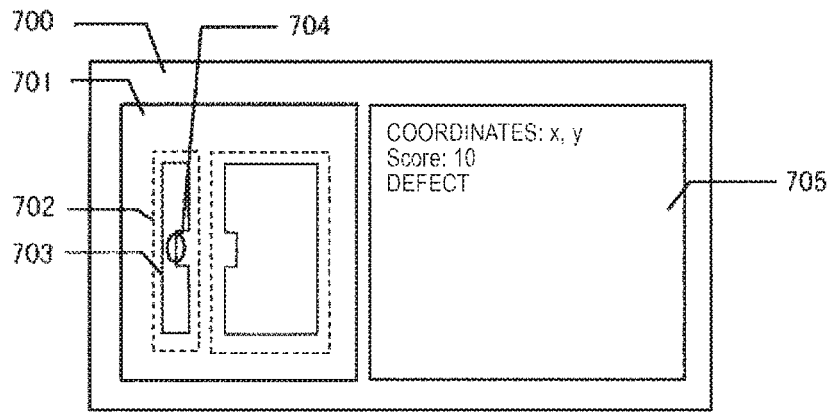

[Fig. 8]
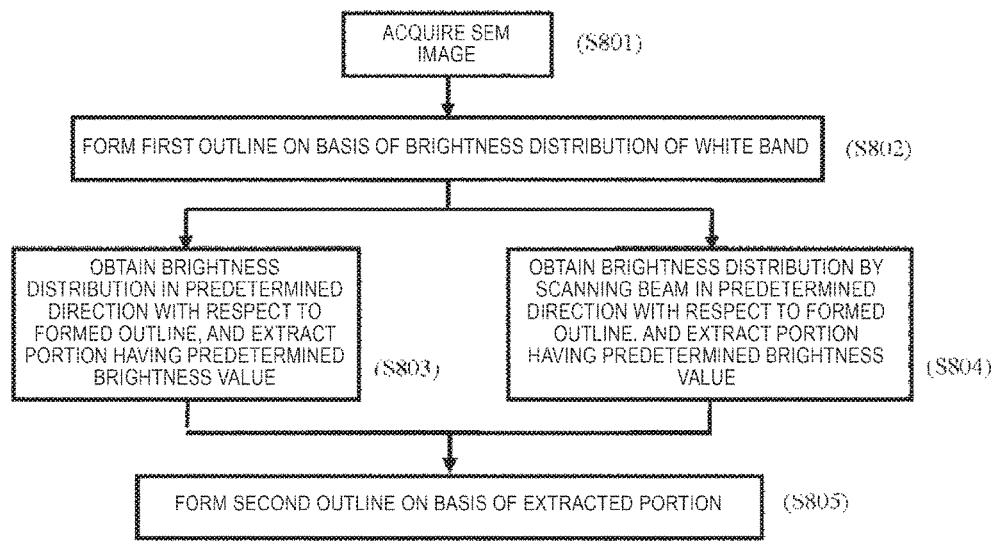
[Fig. 9]
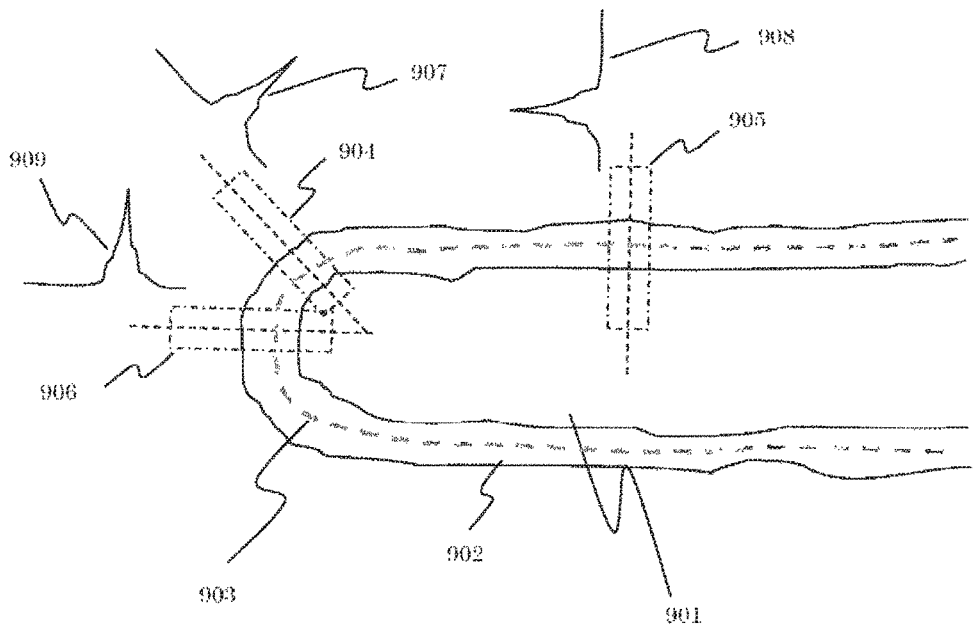

[Fig. 10]
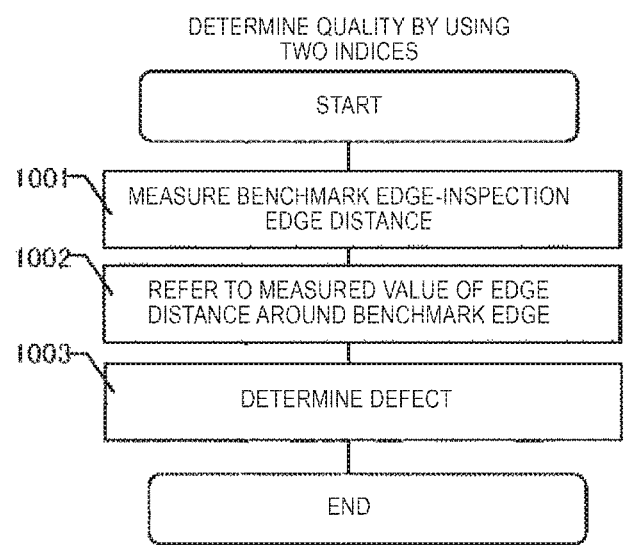

[Fig. 11]
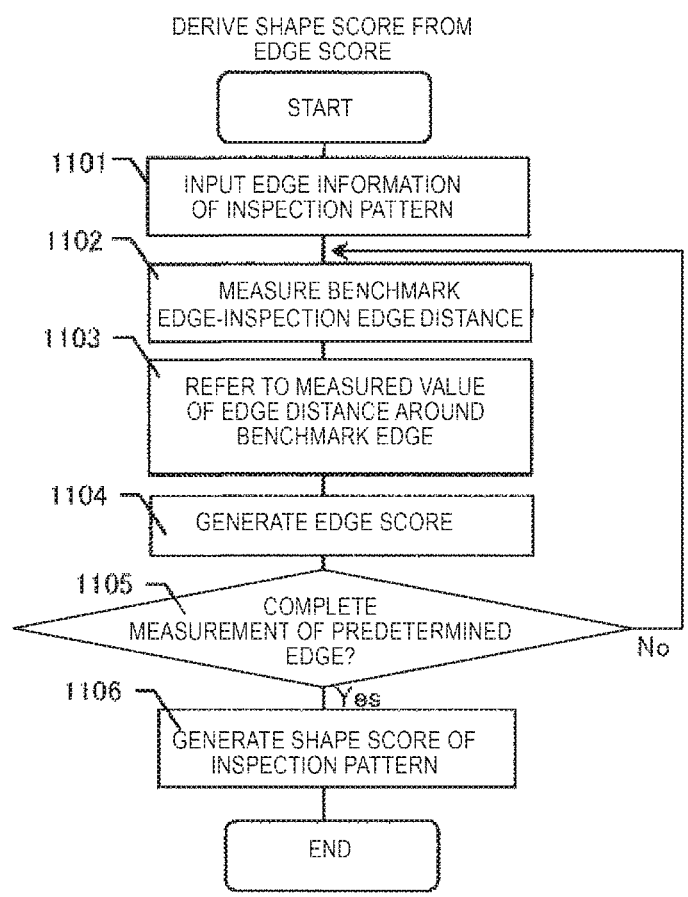

[Fig. 12]
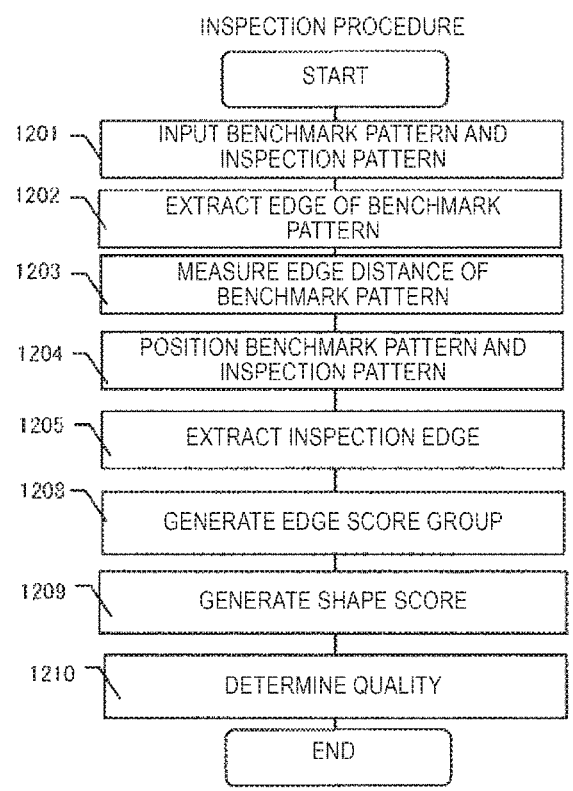

[Fig. 13]
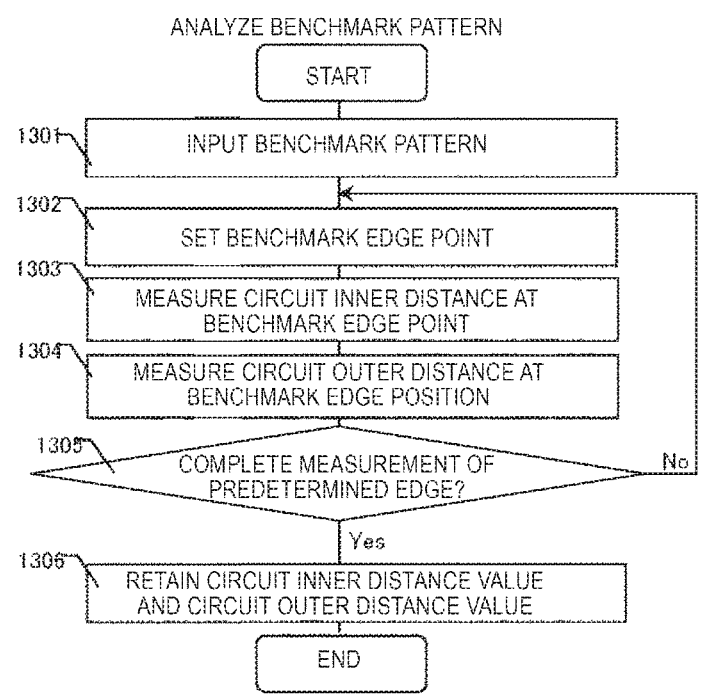

[Fig. 14]
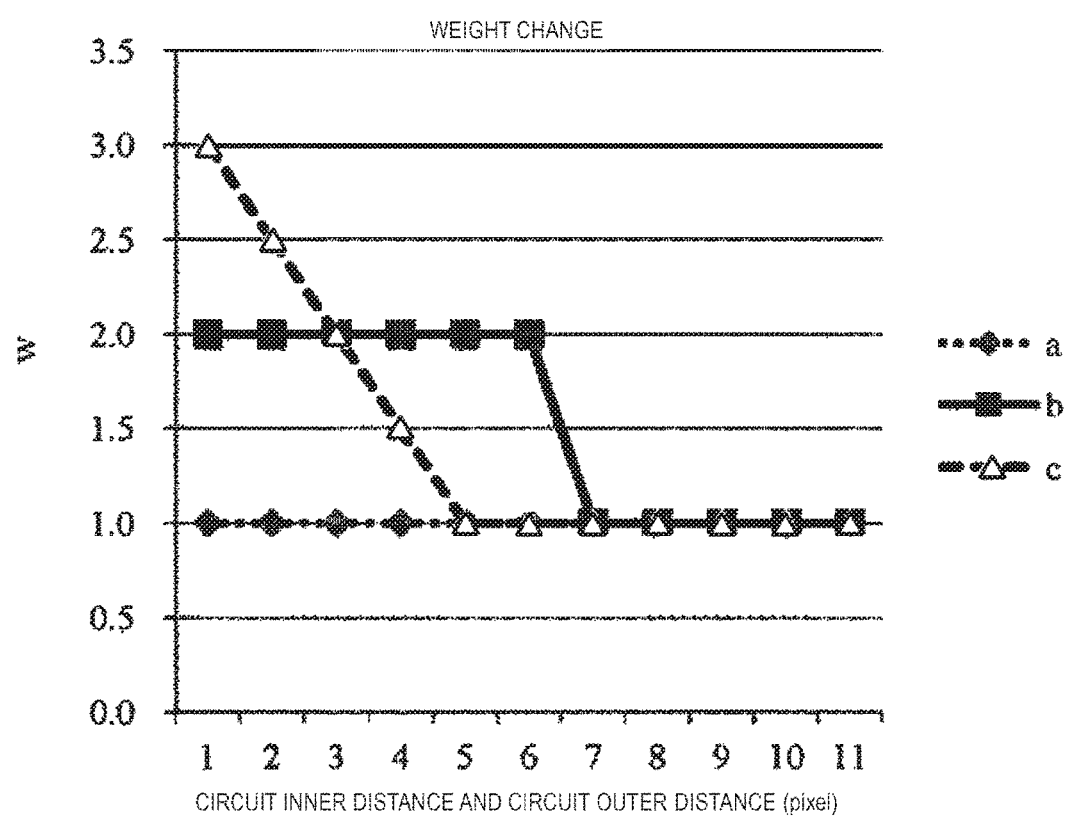

[Fig. 17]
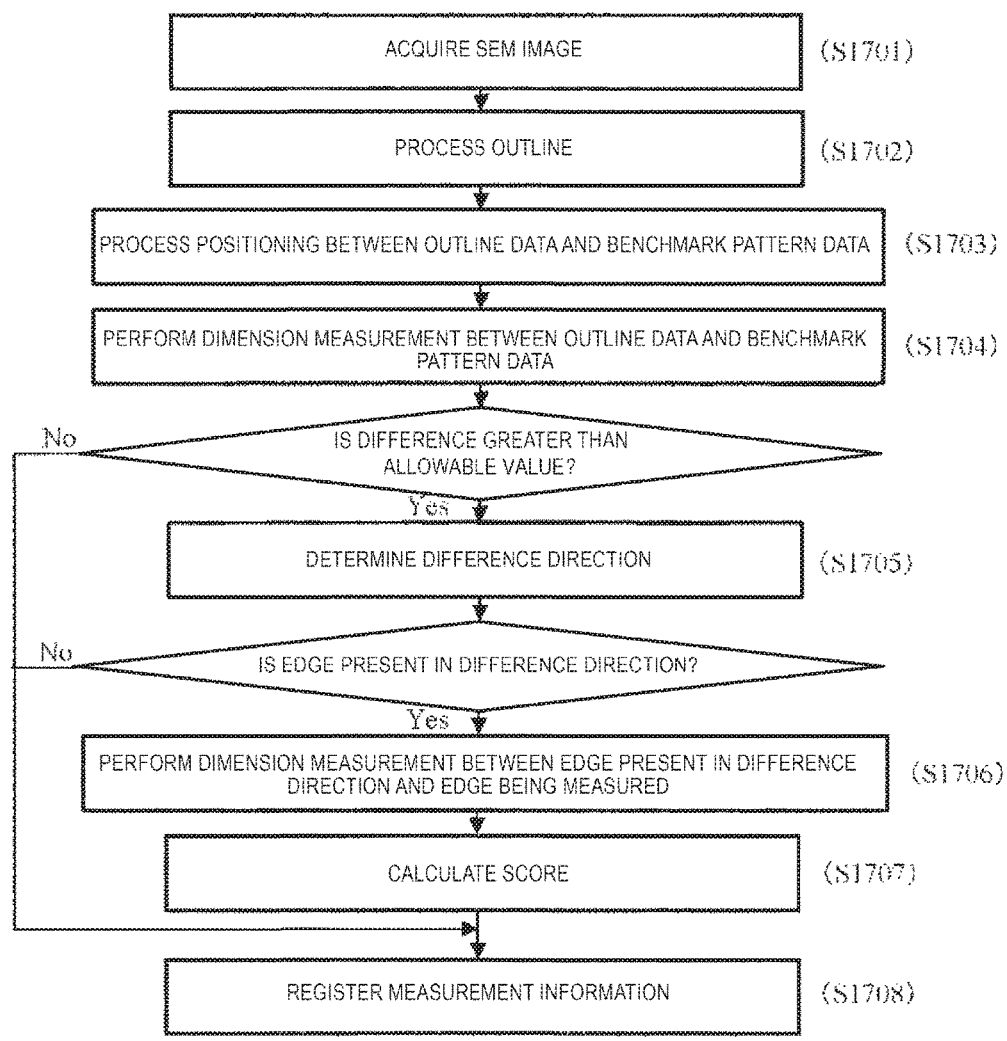

[Fig. 18]
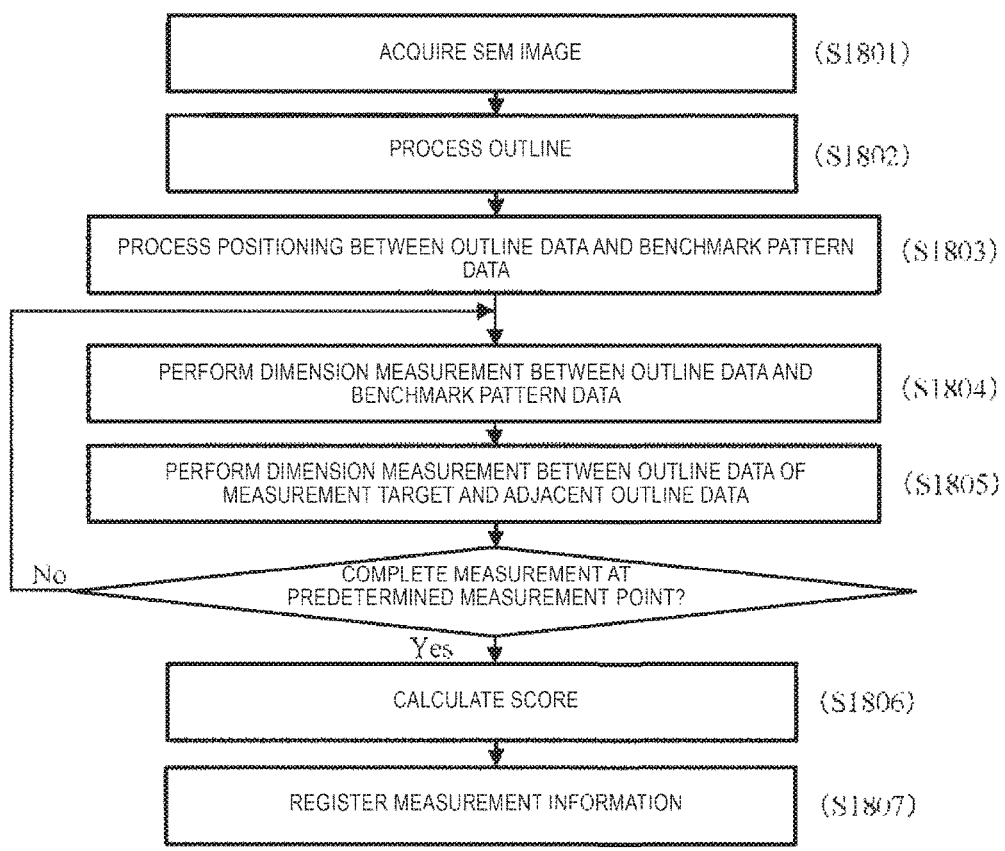

[Fig. 19]
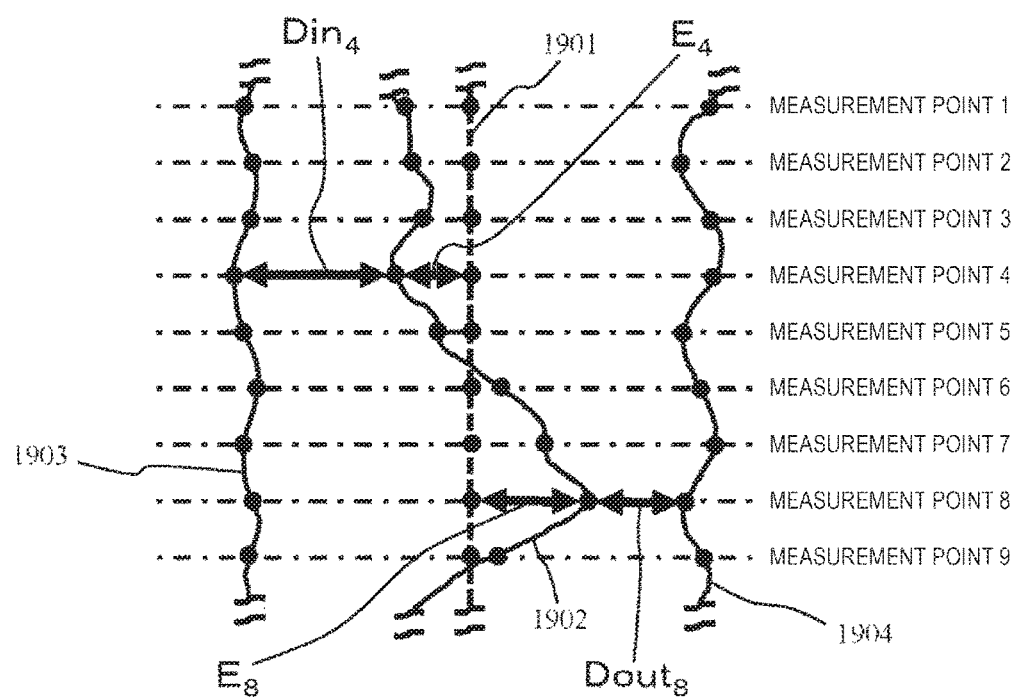

PATTERN-MEASURING DEVICE AND COMPUTER PROGRAM

TECHNICAL FIELD

The present invention relates to a pattern-measuring device and a computer program, and in particular, relates to a pattern-measuring device evaluating the performance of a circuit pattern of an electronic device by comparing the circuit pattern of the electronic device with a benchmark pattern, a computer program, and a semiconductor measurement system.

BACKGROUND ART

Recently, a semiconductor has been microfabricated and multilayered, and the logic has also become complicated, and thus, it is extremely difficult to manufacture a semiconductor. As a result thereof, a defect due to a manufacturing process tends to frequently occur, and it is important to accurately inspect such a defect.

A review scanning electron microscope (SEM) reviewing a defect on the basis of coordinates information of the defect which is detected by an optical inspection device or the like and a critical dimension-SEM (CD-SEM) measuring the dimension of a pattern on the basis of waveform information which is formed on the basis of a detected signal are used for specific inspection or measurement of the defect. The SEM inspection devices inspect a circuit pattern corresponding to inspection coordinates based on simulation of a semiconductor manufacturing process or inspection coordinates based on an inspection result of the optical inspection device. Various inspection methods have been proposed, and in particular, in the semiconductor manufacturing process for forming a pattern having a width of less than or equal to 65 nm, in order to accurately grasp the state of the defect according to an optical proximity effect, a method of detecting a defect by a shape comparison with a benchmark pattern (PTL 1 and PTL 2) or a method of detecting a defect by analysis of a circuit pattern (PTL 3) have been proposed.

CITATION LIST

Patent Literature

PTL 1: JP-A-2004-163420 (corresponding to U.S. Pat. No. 8,045,785)
PTL 2: JP-A-2007-248087 (corresponding to U.S. Pat. No. 8,019,161)
PTL 3: JP-A-2002-148031

SUMMARY OF INVENTION

Technical Problem

It is difficult to transfer a circuit pattern to a wafer according to design data as microfabrication progresses. For this reason, it is considered that allowing a shape deformation in a portion which does not affect the operation of a semiconductor device and strictly inspecting a shape deformation in a portion which affects the operation of the semiconductor device as a defect will be required in the future. In particular, changing an inspection benchmark in a portion in which the density of the circuit pattern is high and a portion in which the density of the circuit pattern is low is required. In a case where the comparison inspection as disclosed in PTL 1 and PTL 2 is performed, any portion of the circuit pattern is inspected by the same benchmark, and thus, in particular, there is a possibility of erroneously determining the shape deformation in the portion which does not affect the operation of the semiconductor device as a defect.

In addition, in PTL 3, a distance between edges of circuit patterns is able to be used in inspection, but a comparison with a benchmark pattern is not performed, and thus, there is a case in which a defect such as an uniform increase or decrease in the distance of the circuit pattern according to a problem in a semiconductor manufacturing device is not able to be detected.

Hereinafter, a pattern-measuring device for quantitatively evaluating an influence due to the presence of a defect or for performing measurement or inspection with high efficiency according to the influence due to the presence of the defect and a computer program are provided.

Solution to Problem

A pattern-measuring device, including: an arithmetic device measuring a dimension of a first distance between a first edge of pattern data being measured which is obtained by a charged particle beam device and a second edge corresponding to the first edge of a benchmark pattern corresponding to the pattern being measured, in which the arithmetic device calculates a score of the first edge or the pattern being measured on the basis of a dimension of a second distance between a third edge which is adjacent to the first edge and the second edge and is different from the first edge and the second edge and at least one of the first edge and the second edge, and the dimension of the first distance, and a computer program allowing the processing described above to be executed in a computer are proposed as one aspect for attaining the object described above.

Advantageous Effects of Invention

According to the configuration described above, a defect occurring on a pattern is able to be output as a quantitative evaluation result according to an influence applied to a circuit.

BRIEF DESCRIPTION OF DRAWINGS

FIG. 1 is a flowchart illustrating a procedure of inspecting a circuit pattern by comparison between a benchmark pattern and a pattern edge.

FIG. 2 is a diagram illustrating a configuration of a semiconductor measurement system.

FIG. 4 is a diagram for illustrating a measurement procedure.

FIG. 5 is a diagram illustrating a specific configuration of the semiconductor measurement system.

FIG. 6 is a flowchart illustrating the measurement procedure.

FIG. 7 is a diagram illustrating a screen of an inspection result.

FIG. 8 is a flowchart illustrating an extraction procedure of an outline.

FIG. 9 is a diagram for illustrating the extraction procedure of the outline.

FIG. 10 is a flowchart illustrating a procedure for obtaining an edge score.

FIG. 11 is a flowchart illustrating a procedure for obtaining a shape score.

FIG. 12 is a flowchart illustrating a quality determination procedure of the circuit pattern.

FIG. 13 is a flowchart illustrating an analysis procedure of the benchmark pattern.

FIG. 14 is a diagram illustrating a relationship between a distance between the inside and the outside of the circuit and a weight used for score calculation.

FIG. 17 is a flowchart illustrating a step of scoring a defect state on the basis of a comparison between design data and outline data.

FIG. 18 is a flowchart illustrating a step of calculating a score of a pattern being measured.

FIG. 19 is a diagram illustrating an example in which a minimum pattern distance or a minimum space distance is obtained by using benchmark pattern data and outline data (pattern data being measured).

DESCRIPTION OF EMBODIMENTS

Figure 3A:
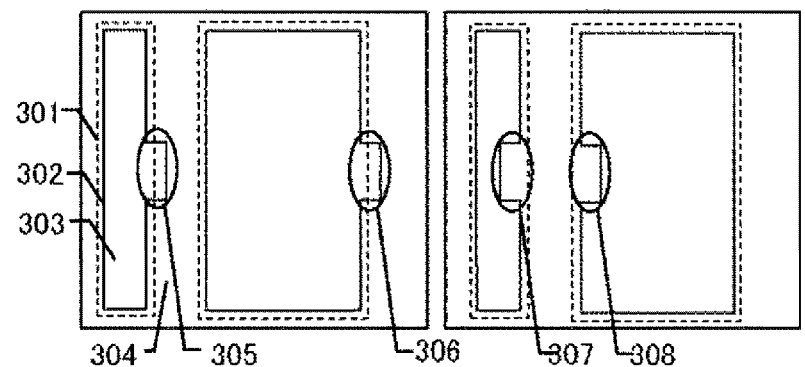
FIGS. 3A and 3B are a diagram in which the benchmark pattern is superimposed on the circuit pattern having a shape deformation.

Hereinafter, a semiconductor measuring device (a pattern-measuring device) will be described in which an error between patterns which is obtained by a comparison between a benchmark pattern and a circuit pattern is evaluated on the basis of the size of a circuit included in the benchmark pattern or a distance with respect to the adjacent circuit, and thus, quality determination of the circuit pattern suitable for an arrangement state of the circuit is performed.

Examples described below mainly relate to a pattern-measuring device which detects a defect by a shape comparison between edge information and a benchmark pattern. In a procedure of detecting a defect, first, an inspection operator defines a circuit pattern having a preferred shape as a benchmark pattern. A circuit pattern generated by simulating design data or a circuit pattern which is actually manufactured, a golden pattern selected by the inspection operator from the manufactured circuit pattern, and the like are used as the benchmark pattern. Next, an edge of the circuit pattern is extracted from a captured image by using edge detection processing or the like. Next, the edge of the benchmark pattern is superimposed on the circuit pattern. The superimposition is performed by using a manual adjustment method or an automatic adjustment method of pattern matching.

The shape of the circuit pattern is deformed into various shapes according to manufacturing conditions of a semiconductor or circuit layout. For this reason, in order to accurately grasp the degree of the deformation, a measurement region is set in a two-dimensional region including inspection coordinates, and a distance between the benchmark pattern and the edge of the circuit pattern (hereinafter, referred to as an edge error) included in the measurement region is comprehensively measured at each point set on the circuit pattern at a predetermined distance. Next, a representative value or an average value of a plurality of edge errors obtained from the measurement region is set to a measured value of the measurement region, and the normality or the defect of the circuit pattern is determined by a comparison with a predetermined threshold value.

In addition, defect detection not using the benchmark pattern is performed by the following procedure. First, a pattern edge is extracted from a captured image of a circuit pattern, and a distance of the pattern edge included in the image is comprehensively measured. Next, a region of the captured image is divided according to a distance value thereof. Next, a defect is detected at each divided region by using an inspection parameter corresponding to the distance value. In a case where the density of the circuit pattern increases, a defect easily occurs, and thus, inspection accuracy increases by changing an inspection method according to the distance of the pattern edge.

On the other hand, a measurement result obtained by the measurement method as described above is an index value indicating the degree of a deformation in the pattern, but the meaning of the index value of the pattern deformation is changed according to the surrounding situation in which the deformation is present. For example, even in a case where the pattern deformations may be identical to each other, an influence applied to the circuit is changed according to the arrangement of surrounding patterns or the like. Therefore, in the examples described below, a pattern-measuring device calculating an index value which quantitatively evaluates an influence applied to such a circuit will be described.

In this example, a pattern-measuring device will be described in which an error in an edge position with respect to a benchmark pattern is mainly measured by a comparison between a circuit pattern of an electronic device and the benchmark pattern, and the error in the edge position is evaluated on the basis of the size of a circuit included in the benchmark pattern or a distance with respect to the adjacent circuit, and thus, quality determination of a suitable circuit pattern according to an arrangement state of the circuit is able to be performed. More specifically, a semiconductor measuring device will be described in which an edge error obtained from a comparison between a captured image and the benchmark pattern by using a circuit size and a circuit distance of a benchmark pattern is scored, and the score is compared with a predetermined threshold value, and thus, the presence or absence of a defect is determined.

EXAMPLE 1

Hereinafter, specific examples of a pattern measuring device and a semiconductor measurement system will be described by using the drawings.

FIG. 2 is a diagram illustrating an outline of a semiconductor measurement system. The semiconductor measurement system is configured of a scanning electron microscope 201 (hereinafter, referred to as SEM) which acquires image data of a circuit pattern and a control device 214 which inspects the circuit pattern by analysis of the image data. SEM 201 irradiates a sample 203 on which an electronic device is manufactured, such as a wafer, with an electron beam 202, traps an electron emitted from the sample 203 by a secondary electron detection unit 204 or reflective electron detection units 205 and 206, and converts the electron into a digital signal by an A/D converter 207. The digital signal is input into a control device 214 and is stored in a memory 208, image processing is performed by a CPU 209 or an image processing hardware 210 such as ASIC or FPGA according to the purpose, and the circuit pattern is inspected.

Further, the control device 214 is connected to a display 211 provided with an input unit, and has a function such as graphical user interface (GUI) which displays an image, an inspection result, or the like with respect to a user. Furthermore, a part or all of the control of the control device 214 is able to be processed and controlled by being allocated to a CPU, an electron calculator mounting a memory which is able to accumulate images thereon, or the like. In addition, the control device 214 is connected to a captured recipe preparing device 212 which manually prepares a captured recipe including coordinates of an electronic device necessary for inspection, a template for pattern matching used for inspection positioning, capturing conditions, and the like, or prepares the captured recipe by using design data 213 of the electronic device, through a network, a bus, or the like.

FIG. 5 is a diagram more specifically illustrating an arithmetic processing device which is embedded in the control unit 214. The semiconductor measurement system exemplified in FIG. 5 includes a scanning electron microscope main body 501, a control device 504 which controls the scanning electron microscope main body, an arithmetic processing device 505 which transmits a control signal to the control device 504 on the basis of a predetermined operation program (recipe) and executes shape evaluation of a pattern from the signal (a secondary electron, a backward scattering electron, or the like) obtained by the scanning electron microscope, a design data storage medium 515 storing design data of a semiconductor device, a designing device 516 which performs preparation of the design data, correction of the design data using simulation, and the like, and an input and output device 517 which inputs predetermined semiconductor evaluate conditions or outputs a measurement result or a defect determination result.

The arithmetic processing device 505 functions as a data processing device for evaluating the shape of the pattern from an obtained image. The control device 504 controls a sample stage or a deflector in the scanning electron microscope main body 501 on the basis of an instruction from a recipe execution unit 506, and executes positioning a scanning region (a field of view) to a desired position. A scanning signal according to a setting magnification or the size of the field of view is provided to a scanning deflector 502 from the control device 504. The scanning deflector 502 changes the size of the field of view (the magnification) to a desired size according to the provided signal.

An image processing unit 507 included in the arithmetic processing device 505 includes an image processing unit 507 processing an image obtained by arranging a detection signal of a detection unit 503 synchronously with the scanning of the scanning deflector 502. In addition, a memory 509, in which a necessary operation program or image data, a measurement result, and the like are stored, is embedded in the arithmetic processing device 505.

In addition, the arithmetic processing device 505 includes a matching processing unit 510 for specifying an evaluation target in the image by using a template stored in advance, as described below, an outline extraction unit 511 extracting an outline from the image data, a benchmark pattern measurement unit 512 measuring a distance between circuits included in a benchmark pattern and a circuit size, a shape evaluation unit 512 obtaining a shape score of a circuit pattern by using the outline and the benchmark pattern obtained from the outline extraction unit 511 and the value of the size of the circuit pattern or the distance from the benchmark pattern measurement unit 512, and a defect determination unit determining the presence or absence of a defect on the basis of a score from the shape evaluation unit 514.

The electron emitted from the sample is trapped by the detection unit 503, and is converted into a digital signal by an A/D converter embedded in the control device 504. Image processing according to the purpose is performed by an image processing hardware embedded in the image processing unit 207, such as CPU, ASIC, FPGA, and the like.

The arithmetic processing device 505 is connected to the input and output device 517, and has a function such as graphical user interface (GUI) which displays an image, an inspection result, or the like with respect to the operator onto a display device disposed in the input and output device 517.

In addition, the input and output device 517 functions as a captured recipe preparing device which manually prepares a captured recipe including coordinates of an electronic device necessary for measurement, inspection, or the like, a template for pattern matching used for positioning, capturing conditions, and the like, or prepares the captured recipe by using the design data stored in the design data storage medium 515 of the electronic device.

The input and output device 517 includes a template preparation unit in which a part of a diagrammatic image formed on the basis of the design data is cut and is formed into a template, and the template is registered in the memory 509 as a template for template matching in the matching processing unit 510. The template matching is a method of specifying a portion in which a captured image which becomes a positioning target is coincident with a template on the basis of coincidence degree determination using a normalization correlation method or the like, and the matching processing unit 510 specifies a desired position of the captured image on the basis of the coincidence degree determination. Furthermore, in this example, the degree of coincidence between the template and the image is expressed by a term such as a coincidence degree or similarity, and the coincidence degree and the similarity are the same from the viewpoint of an index indicating the degree of coincident between the template and the image. In addition, an inconsistency degree or dissimilarity is one aspect of the coincidence degree or the similarity.

In addition, an image integration unit 508 which forms an integrated image by integrating signals obtained by SEM is embedded in the image processing unit 507. In a case where there are a plurality of detection units 503 which complement electrons, an image is prepared in which a plurality of signals obtained by the plurality of detection units are combined. Accordingly, it is possible to generate an image according to an inspection object. In addition, a plurality of images obtained by one detection unit are integrated, and thus, it is possible to generate an image in which a noise included in each of the images is suppressed.

For example, the outline extraction unit 511 extracts an outline from the image data according to a flowchart as illustrated in FIG. 8. FIG. 9 is a diagram illustrating the outline of outline extraction.

First, an SEM image is acquired (Step 801). Next, a first outline is formed on the basis of a brightness distribution of a white band (Step 802). Here, edge detection is performed by using a white band method or the like. Next, a brightness distribution is obtained in a predetermined direction with respect to the formed first outline, and a portion having a predetermined brightness value is extracted (Step 803). Here, it is desirable that the predetermined direction is a direction perpendicular to the first outline. As illustrated in FIG. 9, a first outline 903 is formed on the basis of a white band 902 of a line pattern 901, and brightness distribution acquisition regions (904 to 906) are set with respect to the first outline 903, and thus, brightness distributions (907 to 909) are acquired in the direction perpendicular to the first outline.

The first outline 903 is a rough outline, but illustrates the approximate shape of the pattern, and thus, in order to form a more highly precise outline by using the outline as a benchmark, the brightness distribution is detected by using the outline as the benchmark. The brightness distribution is detected in the direction perpendicular to the outline, and thus, a peak width of a profile is able to be narrowed, and as a result thereof, an accurate peak position or the like is able to be detected. For example, in a case where the positions of peak tops are connected to each other, a highly precise outline (a second outline) is able to be formed (Step 905). In addition, the outline may be formed by connecting predetermined brightness portions to each other without detecting the peak top.

Further, in order to prepare the second outline, a profile is formed by scanning an electron beam in the direction perpendicular to the first outline 903 (Step 904), and the second outline is also able to be formed on the basis of the profile.

FIG. 6 is a flowchart illustrating an inspection procedure of a semiconductor pattern. In this example, an example will be described in which semiconductor measurement is applied to inspection of a portion in which a defect may occur on a wafer which is specified in advance by an appearance inspection device, evaluation of process simulation of a semiconductor, or the like. The portion in which a defect may occur is a portion in which the occurrence of the defect is predicted.

First, an operator sets inspection conditions for capturing and measuring a circuit pattern on the wafer by using the recipe preparing device 212 (Step 601). The inspection conditions are a capturing magnification of the SEM 201, coordinates of the circuit pattern which becomes an inspection target (hereinafter, referred to as inspection coordinates), or the like.

Next, a captured recipe is generated on the basis of the set inspection conditions (Step 602). The captured recipe is data for controlling the SEM 201, and a template for specifying the inspection conditions set by the inspection operator or an inspection position from the captured image is defined. Next, the circuit pattern is captured by the SEM 201 on the basis of the recipe, pattern matching is performed by using a template for positioning, and an inspection point in the captured image is specified (Step 603).

Next, the circuit pattern is measured (Step 604). As described above, an image which becomes a measurement target may be an image generated by combining signals obtained from a plurality of detection units, or may be an image generated by integrating images obtained from one detection unit. Finally, the quality of the circuit pattern is determined by using a measured value of the circuit pattern (Step 605).

Hereinafter, the details of a measurement procedure of the circuit pattern (Step 604) will be described. FIG. 1 is a flowchart illustrating a measurement procedure of a semiconductor pattern, and the measurement procedure is executed by a shape evaluation unit 513. The measurement procedure will be described by using an example of the circuit pattern in FIG. 3 and FIG. 4.

Figure 3B:
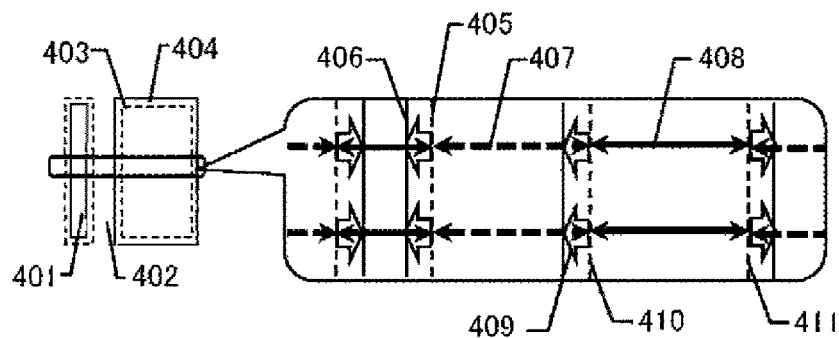

FIG. 3 is a diagram in which a benchmark pattern 301 is superimposed on a captured image of a circuit pattern 302 which is an inspection target. Two adjacent circuits are included in captured images in FIG. 3(A) and FIG. 3(B), respectively. As seen from a comparison with respect to the benchmark pattern 301, convex deformations 305 and 306 are included in the circuit of FIG. 3(A), and concave deformations 307 and 308 are included in FIG. 3(B). The convex deformation is a deformation in which the circuit portion 303 protrudes to a non-circuit portion 304, and causes a short circuit defect in the circuit. In addition, the concave deformation is a deformation in which the circuit portion 303 is recessed, and causes a disconnection defect in the circuit. For the sake of description, the defects 305 to 308 are defects having the same size. In FIG. 3(A), two convex deformations having the same size are included, but influences of the deformations on the circuit are different from each other. As the convex deformation occurs in a portion in which a distance between the adjacent circuits is narrow, the deformation has a bad influence on the circuit.

For this reason, in the example of FIG. 3(A), a defect degree of the convex deformation 305 including the adjacent circuit pattern is higher than that of the convex deformation 306. In contrast, as the concave deformation occurs in a portion in which the circuit size is small, the deformation has a bad influence on the circuit. For this reason, in the example of FIG. 3(B), the defect degree of the concave deformation 307 is higher than that of the concave deformation 308.

In order to derive such a circuit size or such a defect degree which is changed according to the adjacent circuit pattern by a comparison between the circuit pattern and the benchmark pattern, the circuit pattern is measured by the procedure of FIG. 1. The details thereof will be described by using FIG. 4.

FIG. 4 is a diagram in which a circuit pattern 404 is superimposed on a benchmark pattern 403. Furthermore, a circuit portion is 401, and a non-circuit portion is 402. A superimposed position is obtained by matching the benchmark pattern 403 to the circuit pattern 404 in a matching processing unit 510. Furthermore, in a case where the benchmark pattern used for measurement and a template for matching performed at the time of capturing an image are different from each other, the matching between the benchmark pattern 403 and the circuit pattern 404 is performed again, and thus, a superimposed position effective for measurement is able to be specified. In the measurement procedure of FIG. 1, first, a distance 409 (hereinafter, referred to as a shape error value) between an edge configuring the benchmark pattern 403 (hereinafter, referred to as a benchmark edge 405) and an edge configuring the circuit pattern 404 (hereinafter, referred to as an inspection edge 406) is measured (Step 101).

Next, the measured value of the distance 409 refers to a distance value 407 and a distance value 408 (Step 102). The distance value 407 is a distance (a circuit outer distance value) between a benchmark edge 405 on a right side of a pattern on a left side and a benchmark edge 410 on a left side of a pattern on a right side. The distance value 407 corresponds to the dimension of a non-circuit portion (a non-pattern portion). In addition, the distance value 408 corresponds to the dimension between a benchmark edge 410 on a left side of the pattern on the right side and a benchmark edge 411 on a right side of the pattern on the right side.

Both of the distance value 407 and the distance value 408 are values according to the position of a left edge of the pattern on the right side. The weight of the measured value between the benchmark edge on the right edge of the left side pattern and the inspection edge (the degree of divergence with respect to the benchmark edge of the inspection edge) is changed according to the position of the adjacent edge. In this example, a method is proposed in which a score is calculated by referring to benchmark data with respect to an edge adjacent to the inspection edge in which divergence with respect to the benchmark pattern is measured (Step 103), and thus, an index value of the degree of a defect in the inspection edge (the degree of normality) is obtained. According to such a score calculation method, a possibility of allowing a defect such as disconnection or short circuit in the pattern to occur is able to be expressed numerically. The score calculation method will be described below.

Furthermore, the circuit outer distance value, for example, is the dimension between the benchmark edge and the non-circuit portion in a benchmark edge position or a numerical value based on the dimension, and a circuit inner distance value, for example, is the dimension between the benchmark edge and the circuit portion in the benchmark edge position or a numerical value based on the dimension. Here, in the circuit pattern where the circuit pattern is intricately deformed, a value which is suitably measured according to the deformation is desirable, but the value is not limited thereto.

The circuit outer distance value and the circuit inner distance value, for example, may refer to a distance which is obtained by measuring a circuit inner distance and a circuit outer distance with respect to the benchmark edge included in the benchmark pattern in advance before the inspection, and is stored in the memory 509, or may refer to a distance which is measured whenever the benchmark pattern is set. The circuit inner distance and the circuit outer distance, for example, are able to be measured in a procedure illustrated in FIG. 13, and the procedure is executed by the benchmark pattern measurement unit 512.

A measurement procedure of the benchmark pattern of FIG. 13 will be described. First, the benchmark pattern is input (Step 1301). Next, a benchmark edge point configuring the benchmark pattern is set. In a case where the data of the benchmark pattern is an image, the edge of the benchmark pattern is detected by a procedure as illustrated in FIG. 8, and the benchmark edge point is set on the edge (Step 1302). In a case where the benchmark pattern is vector data such as GDS, for example, the benchmark edge point is set on a line segment configuring a circuit by determining a rule such as a distance of 1 nm. Next, the circuit inner distance is measured by referring to the edge of the benchmark pattern which is present around the benchmark edge point (Step 1303). Next, the circuit outer distance is measured by referring to the edge of the benchmark pattern which is present around the benchmark edge point (Step 1304).

In a case where the benchmark pattern is data according to design data such as GDS or process simulation, the information of the circuit portion and the non-circuit portion is defined in the data, and thus, it is possible to easily determine whether a region configuring the benchmark pattern is the circuit portion or the non-circuit portion. However, in a case where the benchmark pattern is image data, it is difficult to determine whether the region is the circuit portion or the non-circuit portion only by the information obtained from the image. In such a case, matching with respect to the design data in which the circuit portion and the non-circuit portion are defined is performed by the matching processing unit 510, a correspondence between the figure of the design data and the figure of the image is obtained on the basis of the matching result, and the information of the circuit portion and the non-circuit portion of the design data corresponds to an image region of the benchmark pattern.

For example, a region surrounded by an edge which is continuous from an edge point A (X1, Y1) to an edge point B (X2, Y2) in image coordinates generates additional information of the image such as the circuit portion, and the circuit inner distance value and the circuit outer distance value are able to be determined on the basis of the additional information.

Furthermore, in a case where it is not necessary to separately evaluate a deformation in the circuit portion from a deformation in the non-circuit portion, the information of the circuit portion and the non-circuit portion is not necessary, and a distance value between the adjacent benchmark edges may be simply measured.

It is confirmed whether or not the measurement of the circuit inner distance and the circuit outer distance is completed with respect to each edge point configuring the benchmark pattern (Step 1305), the circuit inner distance value and the circuit outer distance value are retained in the memory 509 (Step 1306). Next, an index for evaluating the inspection edge (hereinafter, referred to as an edge score) is calculated from a shape error, the circuit inner distance value, and the circuit outer distance value. The edge score, for example, is calculated on the basis of Expressions 1 to 3.

$$\text{Edge Score } 1 = W*E/P \qquad \text{[Expression 1]}$$

$$\text{Edge Score } 2 = W*E/S \qquad \text{[Expression 2]}$$

$$\text{Edge Score } 3 = W*E/R \qquad \text{[Expression 3]}$$

E: Distance (PIXEL, nm, and the like) between Benchmark Edge and Inspection Edge W: Coefficient P: Circuit Inner Distance (PIXEL, nm, and the like) of Benchmark Edge Position or Value based on Circuit Inner Distance S: Circuit Outer Distance (PIXEL, nm, and the like) of Benchmark Edge Position or Value based on Circuit Outer Distance R: Distance with respect to Edge adjacent to Benchmark Edge Position (PIXEL, nm, and the like) or Value based on Distance Expression 1 is used in a case where the inspection edge is present on a circuit inner side of the benchmark pattern. In a case where the inspection edge is present on a circuit outer side, the score is set to 0. That is, the shape error is divided by the value based on the circuit inner distance value or the circuit inner distance value, and thus, the edge score increases as the circuit inner distance decreases. On the other hand, Expression 2 is used in a case where the inspection edge is present on the circuit outer side of the benchmark pattern. In a case where the inspection edge is present on the circuit inner side, the score is set to 0. That is, the shape error is divided by the value based on the circuit outer distance value or the circuit outer distance value, and thus, the edge score increases as the circuit outer distance decreases. Expression 3 is a calculus equation in which the edge score is obtained by not using the information of the circuit inner distance and the circuit outer distance but by using the information of only a simple circuit distance. R is a distance between the benchmark edge and the adjacent edge.

W is a coefficient. A setting example of W according to the circuit inner distance and the circuit outer distance is illustrated in FIG. 14. In a graph a, W is 1.0, and W has an invariably constant value with respect to the circuit inner distance and the circuit outer distance. A graph b is an example in which the value of W is switched in a case where the circuit inner distance and the circuit outer distance are greater than a certain numerical value. This is used in a case where a shape deformation occurring in a portion in which the distance or the size of the circuit pattern is less than or equal to a certain numerical value is particularly strictly evaluated. A graph c is an example in which W is gradually changed according to the circuit inner distance and the circuit outer distance. Thus, it is possible to perform quality determination according to various inspection applications by using W.

As described above, the quality of the inspection pattern is determined by comparing the obtained edge score with a predetermined threshold value (Step 605). Defect determination is performed by the defect determination unit 514. Specifically, each edge score of Expression 1 or Expression 2 is compared with a threshold value which is set separately from the edge score, processing is performed in which in a case where the edge score is greater than or equal to the threshold value, it is determined as a defect, and in a case where the edge score is less than the threshold value, it is determined as normality, and the result thereof is retained in the memory 509.

As described above, when dimension measurement of a first distance between a first edge of pattern data being measured which is obtained by a charged particle beam device and a second edge corresponding to the first edge of a benchmark pattern corresponding to the pattern being measured is executed, the score of the first edge or the pattern being measured is calculated on the basis of the dimension of a second distance between a third edge which is adjacent to the first edge and the second edge and is different from the first edge and the second edge and at least one of the first edge and the second edge, and the dimension of the first distance, and thus, a pattern shape which is able to be a defect is able to be quantitatively evaluated.

In addition, the defect determination is able to be performed by a measurement flow illustrated in FIG. 10. First, a distance between the benchmark edge and the inspection edge is measured (Step 1001). Next, the distance refers to the circuit outer distance and the circuit inner distance (Step 1002). Finally, a defect is determined by comparing the edge distance, the circuit outer distance, and the circuit inner distance with a predetermined threshold value which is set with respect to each of the edge distance, the circuit outer distance, and the circuit inner distance (Step 1003). For example, in a case where the circuit outer distance and the circuit inner distance are less than or equal to 10 pixels, respectively, an inspection edge in which the edge distance is greater than or equal to 5 pixels is determined as a defect, and in a case where the edge distance is greater than 10 pixels, an inspection edge in which the edge distance is greater than or equal to 10 pixels is determined as a defect.

Next, a method will be described in which a score is obtained on the basis of not only the benchmark edge information but also a relationship between an actual pattern adjacent to an edge being measured and the edge being measured. In this example, a pattern distance and a space distance in a field of view (FOV) of a electron microscope are comprehensively measured, an index such as a "minimum pattern distance" and a "minimum space distance" is calculated, and finally, a defect is specified by evaluation combined with the index described above (a weighed score). A calculus equation in which the score increases the measured value between the edges of the inspection patterns decreases is stored in advance in the memory 509 or the like such that the minimum pattern distance and the minimum space distance are able to be reflected to score calculation, and calculation using the stored calculus equation is executed by the shape evaluation unit 513. In the shape evaluation unit 513, for example, the score is calculated on the basis of the following arithmetic expressions.

$$\text{Edge Score } 4=W*E/(P-D\text{in})\quad\text{[Expression 4]}$$

$$\text{Edge Score } 5=W*E/(S-D\text{out})\quad\text{[Expression 5]}$$

E: Distance (PIXEL, nm, and the like) between Benchmark Edge and Inspection Edge W: Coefficient P: Circuit Inner Distance (PIXEL, nm, and the like) of Benchmark Edge Position or Value based on Circuit Inner Distance S: Circuit Outer Distance (PIXEL, nm, and the like) of Benchmark Edge Position or Value based on Circuit Outer Distance Din: Distance of Inspection Edge Configuring Circuit Dout: Distance of Inspection Edge Configuring (Space) between Circuits A specific example of edge score calculation of the arithmetic processing device 505 will be described by using FIG. 18 and FIG. 19. First, an SEM image is acquired by using a scanning electron microscope (Step 1801), and an outline corresponding to an edge portion of the SEM image is extracted (Step 1802). Then, positioning processing is executed between outline data and benchmark pattern data (a benchmark edge) (Step 1803). The positioning processing, for example, may be executed by adjusting at least one position of the outline data and the benchmark pattern data such that a distance between the benchmark edge and the outline is minimized. FIG. 19 is a diagram illustrating an example in which the benchmark pattern data and the outline data are superimposed by positioning the benchmark pattern data and the outline data. A line segment 1901 is a benchmark edge of an edge which becomes a measurement target. In addition, a line segment 1902 is an outline of an edge being measured (an inspection edge), and a line segment 1903 is an outline of the other edge of a pattern to which the edge being measured belongs. The line segment 1902 and the line segment 1903 correspond to a right edge and a left edge of one line pattern, respectively. A line segment 1904 is an outline of a left edge of a pattern adjacent to a line pattern which is formed by the line segment 1902 and the line segment 1903. Furthermore, a benchmark edge corresponding to the line segment 1903 and the line segment 1904 is not illustrated.

Dimension measurement is executed between the benchmark pattern and the outline which are positioned as illustrated in FIG. 19 (Step 1804). In this example, dimension measurement between the line segment 1901 and the line segment 1902 is performed with respect to measurement points 1 to 9, and $E_1$ to $E_9$ are obtained. Further, dimension measurement between an edge (an outline) which becomes the measurement target and an edge (an outline) adjacent to the edge which becomes the measurement target is performed (Step 1805). In this example, the line segment 1902 is the edge which becomes a measurement target, and thus, dimensions ($Din_1$ to $Din_9$) between the line segment 1902 and the line segment 1903, and dimensions ($Dout_1$ to $Dout_9$) between the line segment 1902 and the line segment 1904 are obtained.

Next, Din-E and Dout-E are obtained at each measurement point, and among them, distances having the minimum value are set to the "minimum pattern distance" and the "minimum space distance", respectively. In a case where "Din-E" is calculated, E is positive in a case where the line segment 1902 is on a pattern inner side (a left side in the drawing) with respect to the line segment 1901, and E is negative in a case where the line segment 1902 is on a pattern outer side. In addition, in a case where "Dout-E" is calculated, E is positive in a case where the line segment 1902 is on the pattern outer side (a right side in the drawing)

with respect to the line segment 1901, and E is negative in a case where the line segment 1902 is on the pattern inner side.

In this example, the "minimum pattern distance" is "$Din_4$-$E_4$", and the "minimum space distance" is "$Dout_8$-$E_8$", and thus, a score is calculated on the basis of the values and Expressions 4 and 5 (Step 1806).

The score obtained as described above is a score to which a relationship between the shape of the edge which becomes the measurement target and the adjacent edge is reflected, and thus, becomes an index value accurately indicating a possibility of disconnection or short circuit. Further, the index value is calculated according to not only a distance between edges of the actual patterns (an absolute dimension) but also the degree of divergence with respect to the benchmark pattern, and thus, the risk of a defect is able to be quantitatively evaluated.

Figure 15A:
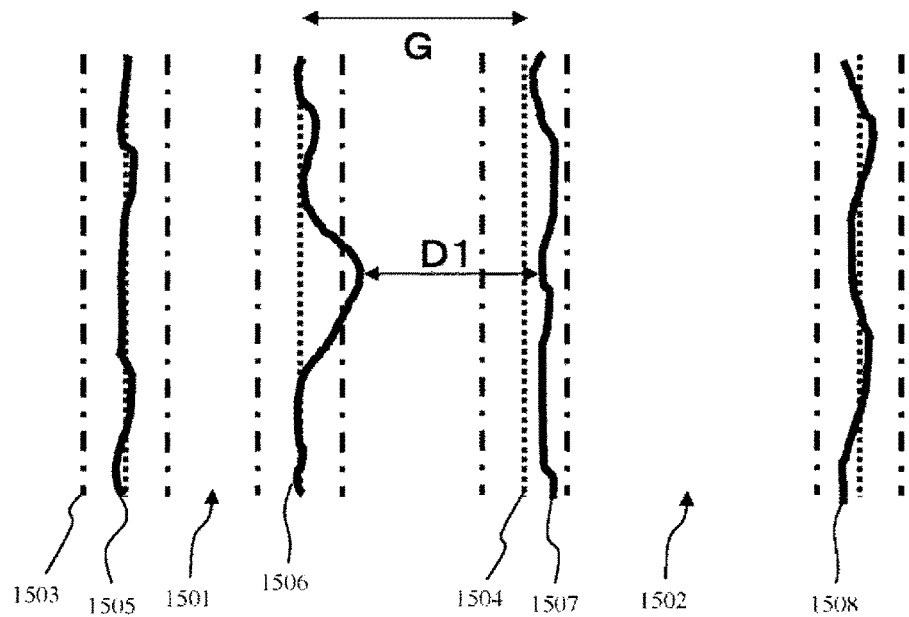
FIG. 15A and 15B are a diagram illustrating a method of setting a possibility of short circuit between patterns to an index value.
Figure 15B:
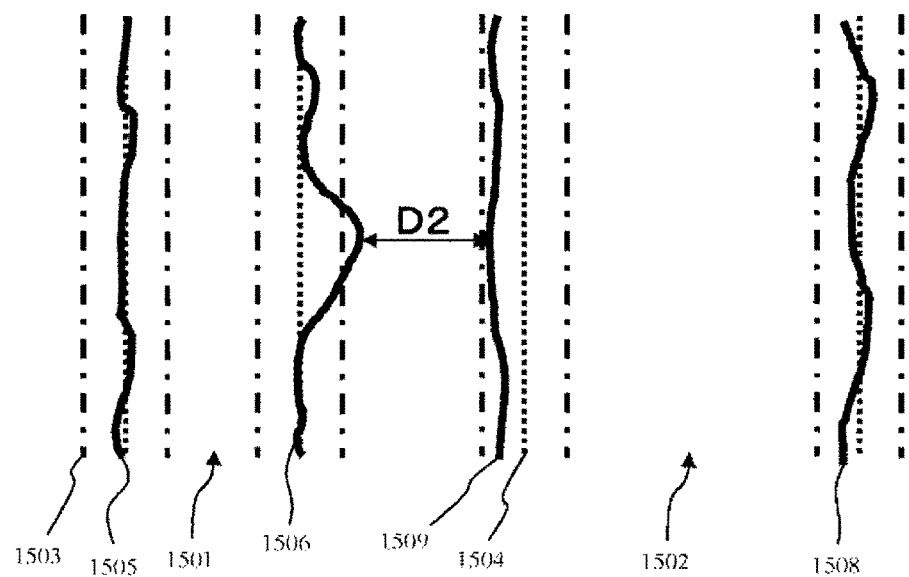

Next, another score calculation method will be described. FIG. 15 is a diagram illustrating a pattern evaluation example of a case where at least two patterns are included in a field of view of SEM, and a deformation is included in one pattern. FIG. 15 illustrates an example in which a narrow pattern 1501 and a wide pattern 1502 are collaterally formed. In addition, a dotted line 1504 indicates design data. In FIG. 15, two edges (dotted lines) are illustrated at each pattern, and an example is illustrated in which positioning is performed between the design data (layout data or simulation data based on the design data) and the outline data obtained from the SEM image.

In FIG. 15(*a*), a left edge 1505 and a right edge 1506 of the narrow pattern 1501, and a left edge 1507 and a right edge 1508 of the wide pattern 1502 are illustrated. Dashed lines (for example, dashed lines 1503) are arranged at a predetermined distance from a dotted line illustrating an edge of the design data, and in this example, in a case where the edge is formed over the dashed line, an edge portion over the dashed line is defined as a defect candidate. In FIG. 15(*a*), an example is illustrated in which a part of the right edge 1506 is formed in the shape of a convex portion of greater than a predetermined threshold value.

Hereinafter, an example will be described in which a portion having a deformation of greater than or equal to a predetermined value and the adjacent edge (in FIG. 15, a left edge of the adjacent pattern) are selectively measured, and thus, efficiency of measurement and a dangerous extent applied to the circuit having a pattern deformation are quantitatively evaluated. In an example of FIG. 15(*a*), the convex portion of the right edge 1506 and the left edge 1507 are separated from each other to a certain degree, but in an example of FIG. 15(*b*), the convex portion of the right edge 1506 and the left edge 1509 are adjacent to each other (D1>D2). This is because the left edge 1509 is formed to be relatively adjacent to the narrow pattern 1501 with respect to the right edge 1507.

Thus, even in a case where the degree of a deformation in the narrow pattern is the same, a possibility of short circuit between patterns is changed according to the edge of the wide pattern. Therefore, in order to evaluate the influence of the deformation of the pattern on the circuit, a distance with respect to the adjacent edge is evaluated with respect to a portion in which a predetermined deformation is observed towards a direction of the deformation, and thus, an index value thereof is obtained. The index value is an index value indicating a possibility of short circuit, and a possibility of a defect is able to be set to a quantitative value.

Figure 16A:
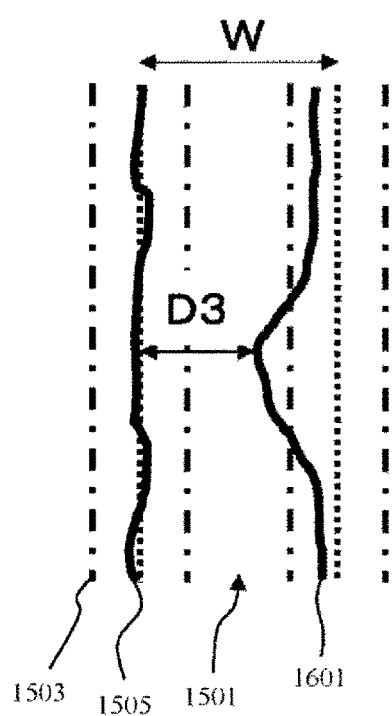
FIG. 16A and 16B are a diagram illustrating a method of setting a possibility of disconnection of a pattern to an index value.
Figure 16B:
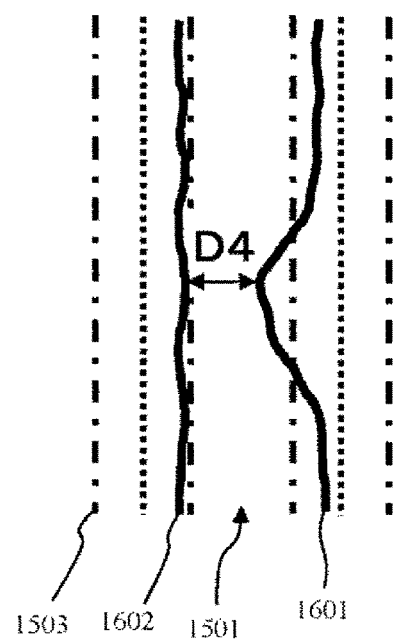

In an example of FIG. 16, an example is illustrated in which the right edge 1601 of the narrow pattern 1501 is narrowed towards the inside. Thus, in a case where a concave portion is formed on the edge, as illustrated in FIG. 16(*a*), it is preferable that a distance (D3) with respect to the left edge 1505 which is an edge of the narrow pattern 1501 on an opposite side is sufficient, but as illustrated in FIG. 16(*b*), in a case where a distance (D4) between the right edge 1601 and the left edge 1602 is short, a possibility of disconnection of the narrow pattern 1501 increases. Therefore, in a case where the concave portion has a size of greater than or equal to a predetermined value (in a case of protruding over a threshold value illustrated by a dashed line), a distance between the edges is measured towards a protruding direction of the portion, and an index value of a possibility of disconnection is obtained on the basis of the measurement result.

According to the configuration described above, a possibility of a circuit defect based on the deformation of the pattern is able to be set to an index value, and efficient circuit evaluation according to the possibility of the defect is able to be performed.

Furthermore, the index value may be a score indicating a distance between edges, a ratio between a distance between edges on design data and a distance between actual pattern edges, or the degree of a distance. In particular, short circuit or disconnection of the pattern is a state where the distance between the edges is zero, and thus, a program may be executed such that a score which increases (or decreases) as the distance shortens is output, and when the score is greater than or equal to a predetermined value (or less than or equal to a predetermined value), a warning indicating that a possibility of short circuit or disconnection increases may be generated.

FIG. 17 is a flowchart illustrating a step of obtaining the index value (the score) which is described by using FIG. 15 and FIG. 16. Steps 1701 to 1704 of FIG. 17 are identical to Steps 1801 to 1804 of FIG. 18 described above. In an example of FIG. 17, an example will be described in which a score is selectively calculated with respect to a measurement point having divergence between an edge of outline data and an edge of benchmark pattern data of greater than or equal to a predetermined value. For example, in the example of FIG. 15, a threshold value illustrated by a dashed line is set to a position separated at a predetermined distance from an edge of a benchmark pattern illustrated by a dotted line, and a relationship with respect to the other edge is selectively evaluated with respect to a portion of greater than the threshold value. In the example of FIG. 15, a part of the right edge 1506 protrudes to a right side (a front side) of the drawing, and thus, it is determined whether or not the other edge on a protruding side is present. It is considered that in a case where the other edge is not present in the adjacent position, a possibility of disconnection or short circuit due to contact between the edges is low.

In a case where the other edge (an edge of the adjacent pattern, or the other edge forming one closed figure along with an edge of a pattern being measured) is present in the direction to which a part of the edge protrudes, dimension measurement between the edge being measured and the other edge is executed (Step 1706). In FIG. 15, dimension measurement between a protruding portion of the right edge 1506 and the right edges 1507 and 1509 is executed. A score is calculated on the basis of the measurement result (Step 1707). In a state of FIG. 15(*b*) in which a distance between the edges is narrow, a possibility of a defect (short circuit) is high, compared to FIG. 15(*a*). Accordingly, the score is calculated by using an arithmetic expression in which the score indicating a possibility of a defect increases as D decreases. In this example, for example, the score is calculated on the basis of Expression 6.

$$\text{Edge Score } 6 = G - D \quad \text{[Expression 6]}$$

G: Distance between Edges on Design Data (Gap between Patterns)

D: Distance between edges adjacent to Protruding Portion (Measured Value)

In addition, as illustrated in FIG. 16, in a case where a score indicating a possibility of short circuit of a pattern is obtained, for example, the score is calculated on the basis of Expression 7.

$$\text{Edge Score } 7 = W - D \quad \text{[Expression 7]}$$

W: Distance between Edges on Design Data (Pattern Width)

D: Distance between edges adjacent to Protruding Portion (Measured Value)

As described above, a score is calculated on the basis of the degree of divergence with respect to benchmark data of an edge which becomes a measurement target, and a dimension value with respect to an edge adjacent to the edge which becomes the measurement target, and thus, a possibility of a defect in a deformed portion of a pattern is able to be quantified.

EXAMPLE 2

FIG. 12 is a flowchart of determining a defect by using a shape score obtained from an edge score. The details thereof will be described. First, a benchmark pattern and an inspection pattern are input (Step 1201). In a case where the benchmark pattern is an image, an edge of the benchmark pattern is extracted (Step 1202). Next, an edge distance of the benchmark pattern is measured, a circuit inner distance and a circuit outer distance are obtained at each edge point (Step 1203). Next, a superimposed position between the benchmark pattern and the inspection pattern is specified by pattern matching or the like (Step 1204). In a case where the inspection pattern is an image, an edge of the inspection pattern is extracted (Step 1205). Next, a distance between an inspection edge point configuring the inspection pattern and a benchmark edge point of a benchmark pattern corresponding to the inspection edge point is entirely measured, and an edge point score at each inspection edge point is obtained by the procedure described in Example 1 (Step 1208). Next, a shape score is obtained from an inspection edge score group (Step 1209).

A procedure in which a shape score is obtained from edge data of the inspection pattern is illustrated in a flowchart of FIG. 11. First, the edge data of the inspection pattern is input (Step 1101). Next, at each edge point configuring the inspection pattern, the distance between the benchmark edge and the inspection edge is measured (Step 1102), the distance refers to the circuit inner distance and the circuit outer distance at the benchmark edge point (Step 1103), and an edge score is generated by using the distance between the edges, the circuit inner distance, and the circuit outer distance (Step 1104). All edge scores of an inspection edge which becomes a measurement target are generated (Step 1105), and then, a shape score is calculated by using an edge score group (Step 1106). The shape score is a numerical value extracted from the edge score. For example, the shape score is the maximum value, the minimum value, the average value, the variance value, the standard deviation, and the like of the edge score group. In addition, the edge scores are arranged in descending order, and the average value of edge scores of the top N may be set as the shape score.

The shape score indicates a two-dimensional shape deformation of the inspection pattern with respect to the benchmark pattern, and the shape score is used in the defect determination, and thus, defect determination based on the two-dimensional shape deformation is able to be performed.

Finally, the shape score is compared with a predetermined threshold value, and the quality of the inspection pattern is determined (Step 1210). In the defect determination, for example, overall determination is able to be performed by comparing the average value calculated from the edge score group with a threshold value in which a plurality of indices such as a standard deviation are separately set.

The measurement of the circuit pattern, the defect determination, or the like, as described above, may be executed by a dedicated hardware, or processing described above or described below may be executed by a general-purpose computer.

REFERENCE SIGNS LIST

201: SEM
202: electron beam
203: sample
204: secondary electron detection unit
205: reflective electron detection unit 1
206: reflective electron detection unit 2
207: A/D converter
208: memory
209: CPU
210: hardware
211: display unit
212: recipe generating system
213: design data
214: control device
300: measurement region
301: benchmark pattern
302: circuit pattern of inspection target
303: circuit portion
304: non-circuit portion
305 to 308: shape deformed portion
401: circuit portion
402: non-circuit portion
403: benchmark pattern
404: circuit pattern of inspection target
405: benchmark edge
406: inspection edge
407: circuit outer distance
408: circuit inner distance
409: distance between inspection edge and benchmark edge
501: scanning electron microscope main body
502: scanning deflector
503: detection unit
504: control device
505: arithmetic processing device
506: recipe execution unit
507: image processing unit
508: image integration unit
509: memory
510: matching processing unit
511: outline extraction unit
512: benchmark pattern measurement unit
513: shape evaluation unit
514: defect determination unit 515: design data storage medium
516: designing device
517: input and output device 517
700: display
701: inspection window
702: benchmark pattern
703: inspection pattern
704: shape deformed portion
705: inspection result window
901: line pattern
902: white band
903: first outline
904 to 906: brightness distribution acquisition regions
907 to 909: brightness distributions in direction perpendicular to first outline

The invention claimed is:

1. A pattern-measuring device, comprising:
an arithmetic device configured to
transmit a control signal to a charged particle beam device to obtain an image of a circuit pattern from the charged particle beam device,
measure a dimension of a first distance between a first edge of pattern data of the image of the circuit pattern obtained by the charged particle beam device and a second edge corresponding to the first edge of a benchmark pattern corresponding to the circuit pattern being measured,
calculate a score of the first edge of the circuit pattern being measured based on a dimension of a second distance between a third edge, which is adjacent to the first edge and the second edge and is different from the first edge and the second edge, and at least one of the first edge and the second edge and the dimension of the first distance,
determine whether a defect is present in the first edge of the circuit pattern based on a comparison between the score and a predetermined threshold value, and
display the score or a value expressing numerically an index about a degree of the defect based on the score.

2. The pattern-measuring device according to claim 1, wherein the arithmetic device calculates the score by using an arithmetic expression described below:

Score=Coefficient×Dimension of First Distance/Dimension of Second Distance.

3. The pattern-measuring device according to claim 2, wherein the arithmetic device calculates the score by using at least one of arithmetic expressions described below:

Score $1=W*E/P$

Score $2=W*E/S$

E: Dimension of First Distance
W: Coefficient
P: Dimension of Second Distance (Width of Benchmark Pattern)
S: Dimension of Second Distance (Distance between Benchmark Patterns).

4. The pattern-measuring device according to claim 1, wherein the arithmetic device calculates the score by using an arithmetic expression described below:

Score=Coefficient×Dimension of First Distance/(Distance between Edges of Benchmark Patterns−Distance between Edges of Patterns being Measured).

5. The pattern-measuring device according to claim 4, wherein the arithmetic device calculates the score by using at least one of arithmetic expressions described below:

Score $1=W*E/(P-D\text{in})$

Score $2=W*E/(S-D\text{out})$

E: Dimension of First Distance
W: Coefficient
P: Dimension of Second Distance (Width of Benchmark Pattern)
S: Dimension of Second Distance (Distance between Benchmark Patterns)
Din: Width of Pattern Being Measured
Dout: Distance between Patterns being Measured.

6. The pattern-measuring device according to claim 1, wherein the arithmetic device obtains a plurality of the scores, and calculates a statistic value of the plurality of scores.

7. A non-transitory computer-readable medium storing a program which, when executed on a computer, causes the computer to:
transmit a control signal to a charged particle beam device to obtain an image of a circuit pattern from the charged particle beam device,
measure a dimension of a first distance between a first edge of pattern data of the image of the circuit pattern obtained by the charged particle beam device and a second edge corresponding to the first edge of a benchmark pattern corresponding to the circuit pattern being measured,
calculate a score of the first edge of the circuit pattern being measured based on a dimension of a second distance between a third edge, which is adjacent to the first edge and the second edge and is different from the first edge and the second edge, and at least one of the first edge and the second edge, and the dimension of the first distance,
determine whether a defect is present in the first edge of the circuit pattern based on a comparison between the score and a predetermined threshold value, and
display the score or a value expressing numerically an index about a degree of the defect based on the score.

* * * * *